: US 10,807,949 B2
(45) Date of Patent: Oct. 20, 2020

(12) United States Patent
Schon et al.

(54) PURIFICATION OF MERCAPTANS OR THIOPHENES USING DIVIDING WALL COLUMN DISTILLATION

(71) Applicant: Arkema Inc., King of Prussia, PA (US)

(72) Inventors: Steven G. Schon, Strafford, PA (US); Rose Aguiar, Meysieu (FR); Jerome Amstutz, Charly (FR); Sylvie Caumia, Tilk (FR); Andrew R. Goddard, Malvern, PA (US); Shashank N. Shah, Allentown, PA (US); Gary S. Smith, Collegeville, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 16/315,689

(22) PCT Filed: Jan. 19, 2017

(86) PCT No.: PCT/US2017/014077
§ 371 (c)(1),
(2) Date: Jan. 7, 2019

(87) PCT Pub. No.: WO2017/127508
PCT Pub. Date: Jul. 27, 2017

(65) Prior Publication Data
US 2019/0282920 A1    Sep. 19, 2019

Related U.S. Application Data

(60) Provisional application No. 62/281,798, filed on Jan. 22, 2016.

(51) Int. Cl.
*B01D 3/14* (2006.01)
*C07C 319/28* (2006.01)
(Continued)

(52) U.S. Cl.
CPC ............ *C07C 319/28* (2013.01); *B01D 3/141* (2013.01); *B01D 3/32* (2013.01); *B01D 3/42* (2013.01);
(Continued)

(58) Field of Classification Search
CPC .......................... B01D 3/41; C07C 319/28–30
See application file for complete search history.

(56) References Cited

U.S. PATENT DOCUMENTS

| 3,049,567 A | 8/1962 | Frantz |
|---|---|---|
| 5,480,665 A | 1/1996 | Smith |

(Continued)

FOREIGN PATENT DOCUMENTS

| GB | 1 268 842 | 3/1972 |
|---|---|---|
| SU | 825515 A1 | 4/1981 |

*Primary Examiner* — Renee Robinson
(74) *Attorney, Agent, or Firm* — Steven D. Boyd (57) ABSTRACT

Aspects of the present invention relate to systems and processes for obtaining desired mercaptans or thiophenes from a feed stream containing a mixture of mercaptans, thiophenes and other components. In one aspect of the invention, a system for separating one or more components from a feed stream of mixed mercaptans includes one or more distillation columns in connection with a feed containing mercaptans, the distillation column having a rectification section, a stripping section, and a feed side section separated from a side draw section by a dividing wall that extends from the rectification section to the stripping section. The distillation column further being in connection with a condenser and a reboiler; and a distillate stream, a side drawn stream, and a bottoms stream.

15 Claims, 5 Drawing Sheets

(51) Int. Cl.
  *B01D 3/32* (2006.01)
  *B01D 3/42* (2006.01)
  *C07C 319/30* (2006.01)
  *C10G 29/28* (2006.01)
  *C10G 7/00* (2006.01)

(52) U.S. Cl.
  CPC .......... *B01D 3/4216* (2013.01); *C07C 319/30* (2013.01); *C10G 7/00* (2013.01); *C10G 29/28* (2013.01)

(56) References Cited

U.S. PATENT DOCUMENTS

| | | |
|---|---|---|
| 5,595,634 A | 1/1997 | Hearn et al. |
| 5,755,933 A | 5/1998 | Ognisty et al. |
| 6,083,378 A | 7/2000 | Gildert et al. |
| 7,670,477 B2 | 3/2010 | Louret et al. |
| 2003/0116474 A1 | 6/2003 | Towler et al. |
| 2004/0204614 A1* | 10/2004 | Groten ................... B01D 3/009 568/38 |
| 2010/0224475 A1* | 9/2010 | Schultz ................ B01D 3/141 202/161 |
| 2012/0048776 A1 | 3/2012 | Podrebarac et al. |
| 2012/0103013 A1 | 5/2012 | King et al. |
| 2013/0068609 A1* | 3/2013 | Bhargava ............... B01D 3/141 203/87 |

* cited by examiner

FIG. 4
PRIOR ART
Conventional 2-Column Sequence

FIG. 5
PRIOR ART

PURIFICATION OF MERCAPTANS OR THIOPHENES USING DIVIDING WALL COLUMN DISTILLATION

CROSS-REFERENCE TO RELATED APPLICATION

This present application is the national phase under 35 USC § 371 of prior PCT International Application Number PCT/US2017/014077 filed Jan. 19, 2017 which designated the United States of America and claimed priority to U.S. Provisional Patent Application Ser. No. 62/281,798 filed Jan. 22, 2016.

FIELD OF THE INVENTION

The invention relates to systems and processes for separating mercaptans or thiophenes from a feed stream to isolate desired compounds.

BACKGROUND OF THE INVENTION

Mercaptans and thiophenes are employed to produce various chemicals useful for industrial applications ranging from production of polymer modifiers to agricultural supplements. Mercaptans with a carbon length of four or greater are typically produced by reacting hydrocarbons, olefins, or alcohols with hydrogen sulfide. These reactions often produce numerous co-products with similar physical properties.

Accordingly, present separation processes for obtaining a desired component from a mixture of mercaptans produced by typical reactions are often extensive, requiring multiple sequential distillation columns. Thus, these separation processes are very expensive. Additionally, various undesired sulfurous organic compounds are often produced by the separation processes due to high temperatures, impurities in the feed, and degradation of the mercaptan products.

In view of the foregoing, there is a need for cost-effective separation processes that reduce the amount of degradation of the mercaptan products.

SUMMARY OF THE INVENTION

Aspects of the present invention relate to systems and processes for separating mercaptans or thiophenes from a feed stream to obtain desired components. In one aspect of the invention, a system for separating one or more components from a feed stream of mixed mercaptans and/or thiophenes includes one or more distillation columns in connection with a feed stream containing mercaptans and/or thiophenes. The distillation column may have a rectification section, a stripping section, and a feed side section separated from a side draw section by a dividing wall that extends from the rectification section to the stripping section. The distillation column may further be in connection with a condenser, a reboiler, a distillate stream, a side drawn stream, and a bottoms stream.

In accordance with another aspect of the invention, a process for separating one or more components from a feed stream of mixed mercaptans and/or thiophenes includes providing one or more distillation columns with a feed stream containing mercaptans and/or thiophenes, the distillation column having a rectification section, a stripping section, and a feed side section separated from a side draw section by a dividing wall that extends from the rectification section to the stripping section; condensing a vapor from the distillation column with a condenser and heating a liquid from the distillation column with a reboiler; removing a distillate stream from a top region of the distillation column; removing a side drawn stream from a side region of the distillation column; and removing a bottoms stream from a bottom region of the distillation column.

In an embodiment of the invention, a distillation column having a divided wall is used to recover as the side draw stream a primary mercaptan with a 4-16 carbon length from a mixture containing its corresponding secondary and/or tertiary mercaptans (with the same number of carbon atoms) and/or other more volatile sulfurous compounds such as sulfides, thiophenes, etc.) and mercaptans with at least one more carbon atom and/or less volatile sulfurous components such as sulfides, thiophenes, etc.

In another embodiment of the invention, a distillation column having a divided wall is used to recover as the side draw stream a secondary mercaptan with a 4-16 carbon length from a mixture containing its corresponding tertiary mercaptan (with the same number of carbon atoms) and/or other more volatile sulfurous compounds such as sulfides, thiophenes, etc., and containing its corresponding primary mercaptan (with the same number of carbon atoms) and/or mercaptans with at least one more carbon atoms and/or other less volatile sulfurous components such as sulfides, thiophenes, etc.

In another embodiment of the invention, a distillation column having a divided wall is used to recover as the side draw stream a tertiary mercaptan with a 4-16 carbon length from a mixture containing its mercaptans with at least one less carbon atom and/or other more volatile sulfurous components such as sulfides, thiophenes, etc., and containing its corresponding primary and/or secondary mercaptan (with the same number of carbon atoms) and/or mercaptans with at least one more carbon atoms and/or other less volatile sulfurous components such as sulfides, thiophenes, etc.

In another embodiment of the invention, a distillation column having a divided wall is used to recover and purify as the side draw stream a cyclic (e.g., saturated and/or unsaturated) mercaptan, most preferably with 4 carbon atoms in the cyclic ring, from a mixture containing more volatile sulfurous components such as, e.g., cyclic unsaturated mercaptan, linear mercaptan etc., and containing less volatile sulfurous components.

In another embodiment of the invention, a distillation column having a divided wall is preferably operated under suitable vacuum to limit the reboiler temperature to less than 240° C. (e.g., to minimize thermal decomposition of the less volatile components, which can produce undesirable byproducts that co-distill with the product). The vacuum pressure is preferably in a range such that the overheads distillate can be condensed with conventional cooling media (e.g., water or air) without requiring chilling or refrigeration.

In another embodiment of the invention, a distillation column having a divided wall is preferably operated at substantially atmospheric pressure (e.g., 760 mm Hg (torr), ±20%) such that the overheads distillate can be condensed with conventional cooling media (e.g., cooling water or cooling air) without requiring a vacuum system, chilling or refrigeration, with a reboiler temperature less than 240° C.

In another embodiment of the invention, the sections of the distillation column on either side of the dividing wall may or may not have an equal cross-sectional area and may vary along the height of the dividing wall. The dividing wall may be configured to accommodate the hydraulic traffic in the sections of the distillation column adjacent to the dividing wall so that each section operates in the optimal hydraulic loading range (percentage of flooding flows) and preferably so that the sections are within the same hydraulic loading range, in terms of percentage of flooding flows, thereby efficiently utilizing the column capacity.

In another embodiment of the invention, the distillation column uses structured packing to provide the requisite number of theoretical stages, in order to minimize the pressure drop regions and/or sections of the distillation column, to ensure that the bottoms vacuum is sufficiently deep to limit the reboiler temperature to less than 240° C., while allowing a milder vacuum in the condenser to facilitate condensation of the distillate with un-chilled conventional cooling media. Another advantage of this embodiment is that the structured packing minimizes residence time and hence the thermal exposure history, further minimizing the possibility of thermal degradation. The structured packing may have different specific surface areas ($m^2$ of contact surface/$m^3$ of structured packing volume) and bed length in various sections of the column to provide the requisite number of theoretical stages while balancing the pressure drops on either side of the dividing wall and maintaining the hydraulic traffic within the optimal ranges throughout the distillation column.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. According to common practice, the various features of the drawings are not drawn to scale unless otherwise indicated. To the contrary, the dimensions of the various features may be expanded or reduced for clarity. Included in the drawings are the following figures.

DETAILED DESCRIPTION OF THE INVENTION

The present invention relates to systems and processes for separating feed streams containing a mixture of mercaptans or thiophenes to recover desired components. Aspects of the present invention may be particularly suited for recovering primary mercaptan, secondary mercaptan, tertiary mercaptan, cyclic mercaptan, olefins, unreacted hydrocarbons, alcohol compounds, and analogues thereof. Systems and processes of the present invention provide improved operational control of separation processes, require a reduced number of equipment, provide lower operating costs, and yield a higher concentration of desired products.

Figure 1:
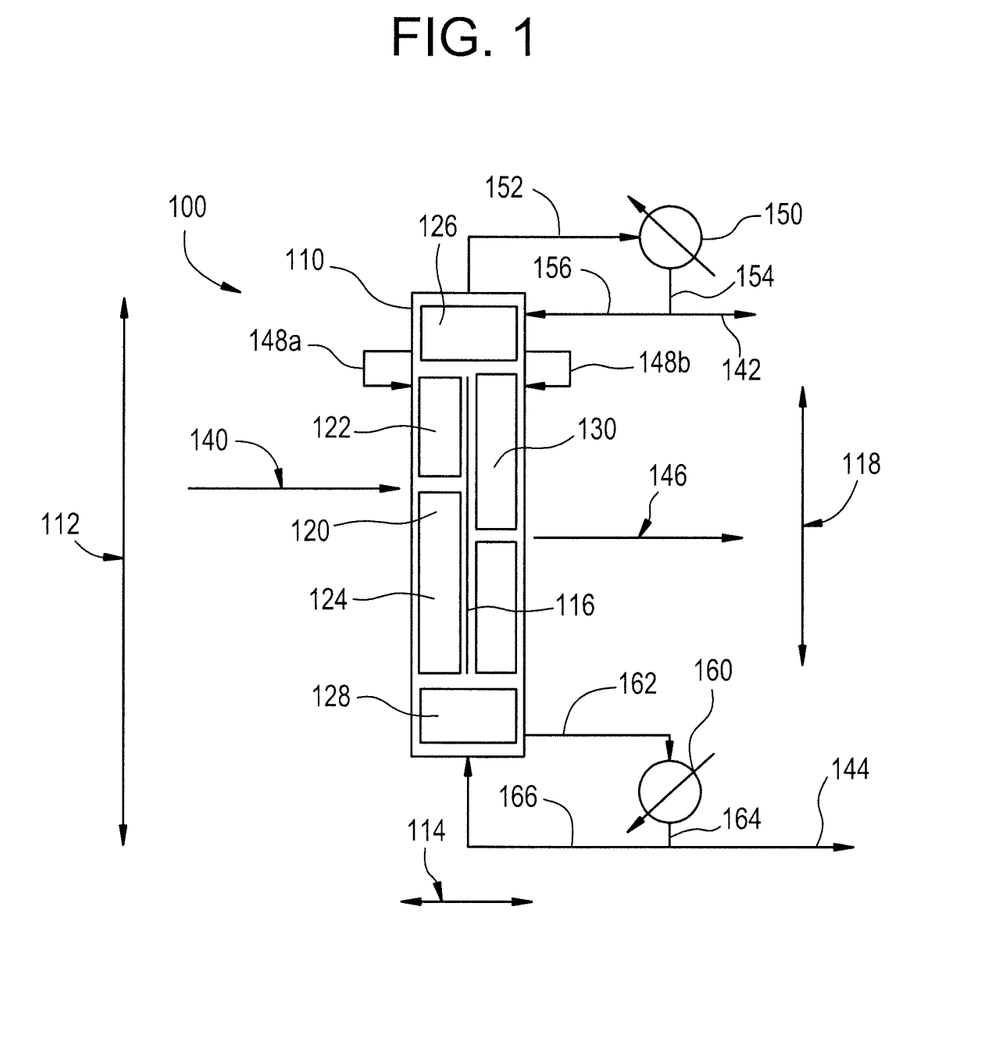
FIG. 1 depicts a system for separating compounds from a mixture of mercaptans or thiophenes in accordance with aspects of the present invention.

With reference to FIG. 1, system 100 may be employed to obtain desired components (e.g., mercaptans and/or thiophenes) from a feed stream containing mixtures of mercaptans. Suitable mixtures of mercaptans or thiophenes for separation by system 100 may be obtained from any process or reaction known by one of skill in the art including, e.g., reactions between hydrocarbons, olefins, or alcohols with hydrogen sulfide. In one embodiment, mixtures of mercaptans or thiophenes are obtained from a reaction of olefin or alcohol with hydrogen sulfide, wherein during the reaction the olefin or alcohol is in stoichiometric excess relative to the hydrogen sulfide.

As a general overview, system 100 includes a distillation column 110 in connection with a feed stream 140, a distillate stream 142, a bottoms stream 144, and a side drawn stream 146. System 100 further includes a condenser 150 and a reboiler 160 that are in fluid communication with column 110. Although system 100 is configured for continuous distillation, in at least one embodiment, column 110 may be configured for batch distillation.

Column 110 includes a dividing wall 116 that extends between opposing sides of an inner surface along height 112 of column 110. Although dividing wall 116 is depicted as extending from rectification section 126 to stripping section 128 in column 110, in at least one embodiment, the dividing wall may extend through the rectification or stripping section and may connect to an inner surface of the top or bottom of the distillation column. Desirably, the composition from one side of dividing wall 116 cannot pass horizontally to the other side of dividing wall 116 and must instead travel either over or under dividing wall 116. Dividing wall 116 divides the central portion of column 110 into two or more sections (e.g., feed side section 120 and side draw section 130), which may have different cross-sectional areas, e.g., between 51% and 85% or between 55% and 65% of the cross-sectional area of column 110 may be allocated to one side of the dividing wall. Additionally or alternatively, dividing wall 116 may be configured such that a region above the connection with feed stream 140 has a larger cross-sectional area than a region below the connection with feed stream 140. In one embodiment, the region above feed stream 140 in feed side section 120 is about 35% of the cross-sectional area of column 110, while the region above the side draw stream 146 in side draw section 130 is about 60% of the cross-sectional area of column 110. Dividing wall 116 may be configured concentrically or as a flat plane. If configured concentrically, either the annular section or the central zone can function as the feed side section 120, with the area on the other side of the concentric wall serving as the side draw section 130.

The height 118 of dividing wall 116 may depend on height 112 of column 110 or on the theoretical number of stages employed within column 100. For example, dividing wall 116 may extend more than 45% and less than 80% of one or more theoretical stages of column 110. Preferably, dividing wall 116 extends more than 55% and less than 70% of the theoretical stages of column 110 or more than 60% and less than two thirds of the theoretical stages of column 110. Additionally or alternatively, height 118 of dividing wall 116 may be between 5% and 95% of height 112 of column 110. In one embodiment, height 118 of dividing wall 116 is between 35% and 80% of height 112 of column 110. In another embodiment, height 118 of dividing wall 116 is between 45% and 70% of height 112 of column 110.

Column 110 may be a tray column, a packed column, a combination of trays and packing, or may include any suitable equipment that provides contact between the liquid and vapor phases. Column 110 is configured to have various sections, including but not limited to a feed side section 120, a rectification section 126, a stripping section 128, and a side draw section 130. Each section 120, 126, 128, and/or 130 of column 110 purifies the composition therein by providing contact between the vapor and the liquid portions of the composition therein, thereby facilitating a vapor-liquid equilibrium. As the vapor portion contacts the liquid portion, the more volatile components are concentrated in the vapor portion and the less volatile components are concentrated in the liquid portion. The amount of contact between the vapor and liquid to achieve the desired concentrations of more volatile components in distillate stream 142 and less volatile components in bottoms stream 144 may be determined from the number of theoretical stages. The number of theoretical stages corresponds to a theoretical number of times the vapor portion and liquid portion should reach vapor-liquid equilibrium to achieve the desired concentrations in the distillate and bottoms. One of skill in the art would readily understand how to determine the number of actual trays or height of packed bedding required for section 120, 126, 128, and/or 130 of column 110 based on the descriptions herein and known correlations.

The feed side section 120 is located in a central portion of column 110 and may extend to have a height approximately equal to the height 118 of dividing wall 116. Feed side section 120 contains a feed tray or distributor, adapted to receive the feed composition containing the mixture of mercaptans or thiophenes from feed stream 140. The feed tray or distributor may be positioned in the feed side section 120 at a location that optimizes the separation of the feed composition, such as in a middle region or in the upper half of the feed side section 120. For example, the feed tray or distributor may be positioned within feed side section 120 such that between 10% and 60% of the theoretical stages in feed side section 120 are above the feed tray or distributor. In one embodiment, between 20% and 50% of the theoretical stages in the feed side section 120 are above the feed tray or distributor. In another embodiment, between 30% and 40% of the theoretical stages of the feed side section 120 are above the feed tray or distributor. Preferably, feed side section 120 serves as a pre-fractionator that concentrates the more volatile components of feed stream 140 in the above-feed fractionator section 122 and concentrates the less volatile components in the below-feed fractionator section 124.

Side draw section 130 is also located in a central region of column 110, but is separated from feed-side section 120 by dividing wall 116. Side draw section 130 contains a side draw tray or re-distributor that is in fluid communication with side draw stream 146. The side draw tray or re-distributor may be positioned within side draw section 130 to optimize recovery of the components in side draw stream 146, e.g., the side draw tray or re-distributor may be positioned in a middle region or lower region of side draw section 130. In one embodiment, between 40% and 90% of the theoretical stages in side draw section 130 are above the side draw tray or re-distributor. In another embodiment, between 50% and 75% of the theoretical stages in side draw section 130 are above the side draw tray or re-distributor. In yet another embodiment, between 55% and 65% of the theoretical stages in side draw section 130 are above the side draw tray or re-distributor.

Side draw section 130 may have more or fewer theoretical stages than feed side section 120. To promote the desired flow rates of vapor and liquid in sections 120 and 130, the types and/or geometry of the actual trays and/or packing may be different in sections 120 and 130. Desirably, sections 120 and 130 are configured such that each section 120 and 130 has a similar pressure profile. In one embodiment, side draw section 130 has about the same pressure profile as side draw section 130.

Rectification section 126 is located above dividing wall 116 and receives vapor from feed side section 120 and/or side draw section 130. Rectification section 126 is in fluid communication with condenser 150 by way of streams 152, 156, and 154. The vapor leaving rectification section 126, also called the distillate, is directed towards condenser 150 by way of stream 152. Liquid distillate enters rectification section 126 by way of stream 156. Desirably, the liquid leaving rectification section 126 is controllably distributed to the feed side 120 section and side draw section 130 of column 110, e.g., by collecting the liquid at a bottom region of the rectification section 126 and distributing the liquid through streams 148a and 148b. A majority, e.g., 60%, 70%, 75%, 80%, 85%, 90%, 95% or more, of the liquid leaving rectification section 126 may be distributed to side draw section 130. In one embodiment, less than 20% by volume of the liquid coming from rectification section 126 enters feed side section 120. In another embodiment, less than 10% by volume of the liquid coming from rectification section 126 enters feed side section 120.

Stripping section 128 is located below dividing wall 116 and receives liquid from feed side section 120 and/or side draw section 130. Stripping section 128 is in fluid communication with reboiler 160 by way of streams 162, 164, and 166. Liquid leaving stripping section 128, also called bottoms, is directed to reboiler 160 by way of stream 162. A portion of the bottoms, which have been heated by reboiler 160, return to stripping section 128 by way of steam 166.

The height 112 and width 114 of column 110 may vary greatly depending on the design requirements or desired performance of system 100. For example, to achieve high levels of separation (e.g., high concentrations of the more volatile components in the distillate and high concentrations of the less volatile components in the bottoms), the number of theoretical stages may be increased and/or the amount of reflux of the distillate and/or bottoms may be increased. Increasing the number of theoretical stages, however, generally increases the cost of column 110 as increasing the number of theoretical stages generally increases height 112 of column 110. Similarly, increasing the amount of reflux generally increases the operating cost of system 100 as condenser 150 and reboiler 160 require more energy. Additionally, increasing the reflux ratio may require increasing width 114 of column 110 to accommodate the additional hydraulic traffic within column 110. Column 110 may be configured to achieve the design parameters at minimal costs by optimizing height 112 and width 114. For example, in one embodiment of column 110, the number of theoretical stages is between 1.05-1.25 times the minimum reflux ratio that is required to achieve the desired separation.

Width 114 of column 110 may vary along the entire height 112 of column 110 or along sections 120, 130, 126, and/or 128 to accommodate larger volumes of hydraulic traffic therein. In one embodiment, width 114 may be larger below the feed tray or distributor, e.g., width 114 below the feed tray may be between 20% and 40%, 40% and 60%, 60% and 80%, or 80% or greater than width 114 above the feed tray or distributor. In another embodiment, however, width 114 does not vary along height 112 of column 110.

Condenser 150 may be any type of heat exchanger suitable for condensing vapors. Preferably, condenser 150 is configured to operate at or less than atmospheric pressure. In one embodiment, the vacuum pressure range is such that the coolant utilized by condenser 150 may be a conventional cooling media, e.g., cooling water, air, or the like. Condenser 150 receives distillate in the vapor phase from stream 152 and produces distillate in the liquid phase. The distillate reflux ratio is a ratio of the amount of distillate directed to rectification section 126 via stream 156 to the amount of distillate in distillate stream 142. Any suitable reflux ratio may be employed by system 100 such as, e.g., between 0.05 and 300, between 10 and 40, or between 0.5 and 20. In one at least one embodiment, where the distillate contains low-boiling components, it may be preferable to operate column 110 at elevated pressures, thereby reducing the need to utilize chilled/sub-ambient temperature coolants in condenser 150. Column 110 preferably includes trays when the column 110 is operated at elevated pressures.

Reboiler 160 may include any suitable heat exchanger configured to operate at temperatures less than 300° C. Reboiler 160 may heat the bottoms to a wide range of temperatures depending on the design parameters of system 100 including, e.g., to a temperature between 100° C. and 300° C., 130° C. and 270° C., 160° C. and 240° C., 190° C. and 240° C., etc. Preferably, reboiler 160 heats the bottoms to a temperature of 250° C. or less. In one embodiment, reboiler 160 heats the bottoms to a temperature of less than 200° C.

The operating conditions of system 100 may be adjusted depending on the composition of the feed and the desired mercaptans or thiophenes to be recovered from the feed. For example, where primary mercaptans are the desired product, the primary mercaptans component may be removed by way of side draw stream 146, as primary mercaptans are less volatile than their corresponding secondary and tertiary isomers, which may be removed via distillate stream 142. As another example, where tertiary mercaptans are the desired product, the tertiary mercaptan component may be removed by way of distillate stream 142, as tertiary mercaptans are more volatile than primary and secondary mercaptans, which may be removed via side draw stream 146. As yet another example, where secondary mercaptans are the desired product, the secondary mercaptan component may be removed by way of side draw stream 146, while tertiary isomers may be removed by way of distillate stream 142 and primary mercaptan by way of bottoms stream 144, along with the less volatile components. As a further example, where cyclic mercaptan is the desired product, the cyclic mercaptan may be removed via side draw stream 146, while more volatile and/or light co-products may be removed via distillate stream 150 and less volatile and/or heavy co-products by way of bottoms stream 144. In one embodiment system 100 is configured such that one or more compounds removed from the side drawn stream are selected from the group consisting of primary mercaptans, secondary mercaptans, tertiary mercaptans, cyclic mercaptans, olefins, unreacted hydrocarbons, and alcohol compounds.

System 100 may recover the desired mercaptans or thiophenes in an output stream 142, 146, and/or 146, while employing less than three distillation columns 110. In one embodiment, system 100 utilizes only one distillation column 110. By utilizing fewer distillation columns than traditional methods, system 100 reduces the required capital costs for separating compositions of mercaptans or thiophenes. Furthermore, less total energy is required than for the multi-column system. Additionally, because fewer distillation columns are required, system 100 may be configured such that desired mercaptans or thiophenes components pass through fewer reboilers 160. Preferably, the desired mercaptans or thiophenes components pass through only one reboiler 160 before being recovered. In one embodiment, system 100 is configured such that one or more of the components from the group consisting of primary mercaptans, secondary mercaptans, tertiary mercaptans, and cyclic mercaptans pass through only reboiler 160 prior to being recovered. In another embodiment, system 100 is configured such that one or more of the components from the group consisting of primary mercaptans, secondary mercaptans, tertiary mercaptans, and cyclic mercaptans do not pass through reboiler 160 prior to being recovered. In yet another embodiment, system 100 is configured such that two or more, e.g., three or more, of the components from the group consisting of primary mercaptans, secondary mercaptans, tertiary mercaptans, and cyclic mercaptans do not pass through reboiler 160 prior to being recovered. Additionally or alternatively, system 100 may be configured such that bottoms stream 144 contains high concentrations of less volatile components, such that the bottoms may be recovered without additional distillation processes. In one embodiment, the bottoms pass only through reboiler 160 prior to being recovered.

Because mercaptans or thiophenes are generally thermosensitive, system 100 advantageously enables desired mercaptan or thiophenes to be recovered with minimal degradation. For example, in one embodiment, less than 3% by mass of one or more of the components from the group consisting of primary mercaptans, secondary mercaptans, tertiary mercaptans, and cyclic mercaptans are degraded during separation within system 100. In another embodiment, less than 2% by mass of one or more of the components from the group consisting of primary mercaptans, secondary mercaptans, tertiary mercaptans, and cyclic mercaptans are degraded during separation within system 100. In yet another embodiment, less than 1.5% by mass of one or more of the components from the group consisting of primary mercaptans, secondary mercaptans, tertiary mercaptans, and cyclic mercaptans are degraded during separation within system 100. In yet a further embodiment, less than 1.5% by mass per component of two or more, e.g., three or more, of the components from the group consisting of primary mercaptans, secondary mercaptans, tertiary mercaptans, and cyclic mercaptans are degraded during separation within system 100.

Aspects of the present invention include:

1. A system for separating one or more components from a feed stream of mixed mercaptans using a distillation column, the system comprising:

one or more distillation columns in connection with a feed stream containing mercaptans, the distillation column having a rectification section, a stripping section, and a feed side section separated from a side draw section by a dividing wall that extends from the rectification section to the stripping section;

the distillation column being in connection with a condenser and a reboiler; and a distillate stream, a side drawn stream, and a bottoms stream.

2. The system of claim 1, wherein the feed stream contains compounds obtained from a reaction of olefin or alcohol with hydrogen sulfide.

3. The system of claim 2, wherein during the reaction the olefin or alcohol was in stoichiometric excess relative to hydrogen sulfide.

4. The system of any of the previous claims, wherein one or two distillation columns are utilized.

5. The system of any of the previous claims, wherein one distillation column is utilized.

6. The system of any of the previous claims, wherein compounds sent to the bottoms stream only pass through one reboiler.

7. The system of any of the previous claims, wherein the feed side section acts as a pre-fractionator.

8. The system of claim 7, wherein the feed side section comprises less than 40% of the column cross sectional area.

9. The system of any of the previous claims, wherein more than 90% of the mercaptans pass one or fewer times through one or more reboilers.

10. The system of claim 9, wherein the distillate stream and the side drawn stream together contain the majority of mercaptans from the feed stream.

11. The system of any of the previous claims, wherein the one or more compounds removed from the side drawn stream are selected from the group consisting of primary mercaptans, secondary mercaptans, tertiary mercaptans, cyclic mercaptans, olefins, unreacted hydrocarbons, and alcohol compounds.

12. The system of any of the previous claims, wherein the reboiler is operated at a temperature of 240 degrees Celsius or less.

13. The system of any of the previous claims, wherein the condenser utilizes a coolant, and the coolant is selected from the group consisting of cooling air and cooling water.

14. The system of any of the previous claims, wherein a liquid coming from the rectification section is controllably distributed to the feed side section and the side draw section of the distillation column.

15. The system of claim 14, wherein less than 10% by volume of the liquid coming from the rectification section enters the feed side section.

16. The system of any of the previous claims, wherein a height of the dividing wall is between 35% and 80% of a height of the distillation column.

17. The system of any of the previous claims, wherein the dividing wall extends more than 45% and less than 80% of one or more theoretical stages of the distillation column.

18. The system of any of the previous claims, wherein the dividing wall extends more than 55% and less than 70% of the theoretical stages of the distillation column.

19. The system of any of the previous claims, wherein the dividing wall extends more than 60% and less than two thirds of the theoretical stages of the distillation column.

20. A process for separating one or more components from a feed stream of mixed mercaptans using a distillation column, the process comprising:
providing one or more distillation columns with a feed stream containing mercaptans, the distillation column having a rectification section, a stripping section, and a feed side section separated from a side draw section by a dividing wall that extends from the rectification section to the stripping section;
condensing a vapor from the distillation column with a condenser and heating a liquid from the distillation column with a reboiler;
removing a distillate stream from a top region of the distillation column;
removing a side drawn stream from a side region of the distillation column; and
removing a bottoms stream from a bottom region of the distillation column.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein

EXAMPLES

The following examples are non-limiting embodiments of the present invention, included herein to demonstrate the advantageous results obtained from aspects of the present invention. The examples were generated using the Aspen Plus process simulator program to simulate and/or calculate the processes therein, including but not limited to, vapor-liquid equilibria, energy requirements, liquid and vapor traffic, pressure drop (based on built-in correlations for the various packings), cross sectional areas and/or diameters of various portions of the distillation column, and estimated percentage of flooding capacity.

Example 1—Separation of Feed Stream Containing n-Dodecyl Mercaptan

The objective is to recover n-dodecyl mercaptan (NDM), at a minimum concentration of 99.5% and containing less than 100 ppm of n-tetradecyl mercaptan (NTM), while recovering 99% of the total amount of NDM within the feed. The feed stream contains 89 wt % NDM, 4.9 wt % s-dodecyl mercaptan (SDM), 0.9 wt % NTM, 0.8 wt % dodecene, and 4.4 wt % components with a boiling point higher than NTM ("heavies"). The mass flow rate of the feed stream is 4000 pounds per hour.

Figure 2:
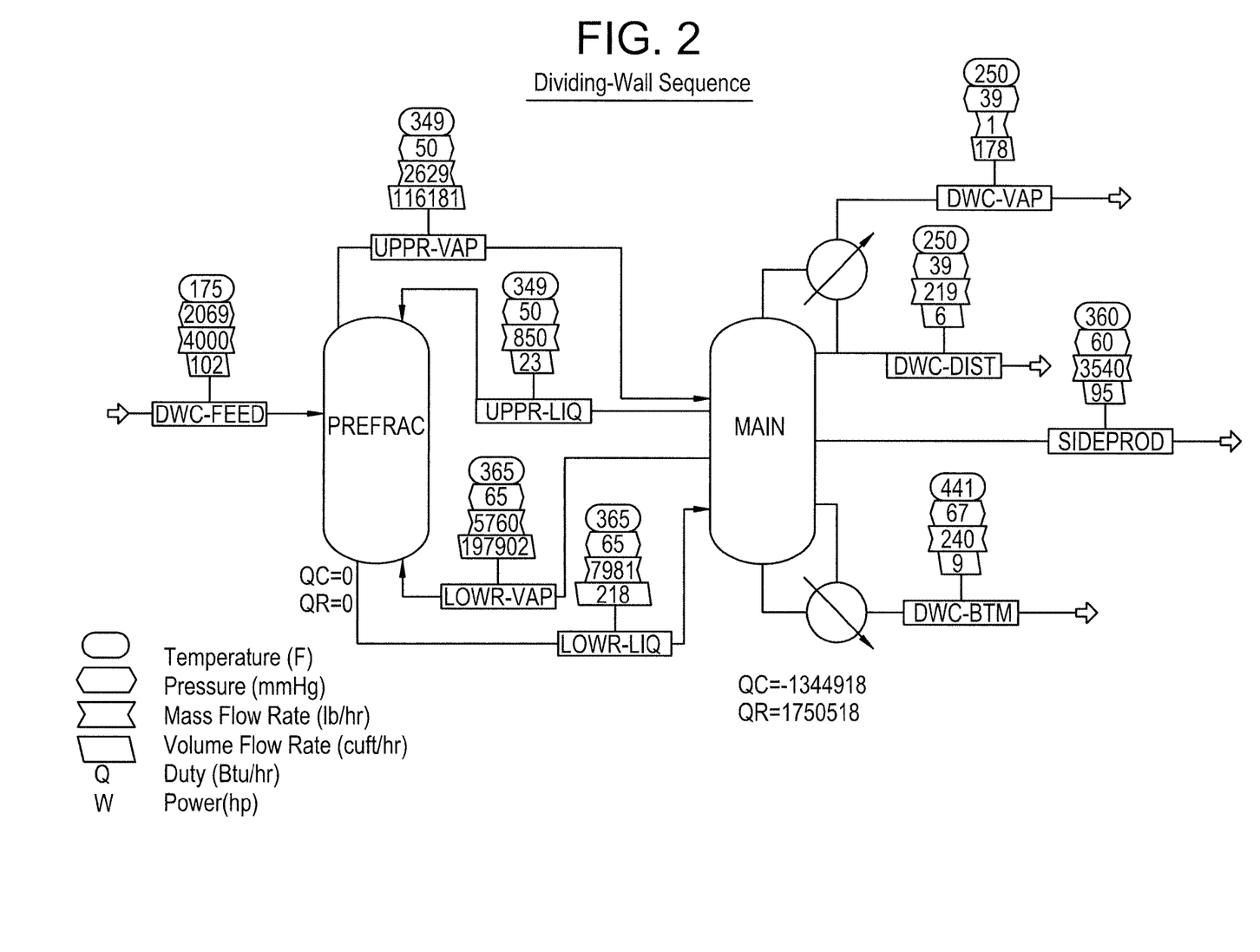
FIG. 2 is a schematic of a system for obtaining n-dodecyl mercaptans from a feed stream containing a mixture of mercaptans and thiophenes according to aspects of the present invention.

A distillation column having a dividing wall is employed in this Example in accordance with aspects of the present invention. The distillation column is modeled as a pre-fractionator column (e.g., without a reboiler or condenser), representing the feed side section of the distillation column having a dividing wall, and a main distillation column having a side draw stream, which represented the dynamics occurring within the other sections of the distillation column having a dividing wall. The model of the distillation column employed herein is illustrated in FIG. 2.

The objectives are achieved by utilizing a system according to aspects of the invention. The system employs a distillation column with the following parameters. The column is specified to be 4 feet in diameter and have 75 total theoretical separation stages, including a reboiler and condenser.

The rectification section has 18 theoretical stages containing Sulzer MellapakPlus 452Y structured packing and a height equivalent to a theoretical plate (HETP) of 13 inches.

The above-feed fractionator section contains 19 theoretical stages of Sulzer MellapakPlus 752Y structured packing with a HETP of 8 inches. The feed side section comprises 36% of the cross sectional area of the distillation column. The region of the side draw section that is above the feed stream contains 19 theoretical stages of Sulzer MellapakPlus 252Y structured packing with a HETP of 16 inches.

The region below the feed stream and above the side draw stream in both of the feed side section and side draw section contains 16 theoretical stages. In both the feed side section and side draw section, the theoretical stages utilize Sulzer MellapakPlus 252Y structured packing with a HETP of 16 inches. The feed side section comprises 42% of the distillation column's cross sectional area in this region.

The region below the feed stream and side-draw stream in both the feed side section and the side draw section contains 15 theoretical stages. In both the feed side section and side draw section, the theoretical stages utilize Sulzer MellapakPlus 252Y structured packing, with a HETP of 16 inches. The feed side section in this region comprises 50% of the cross sectional area of the distillation column.

The stripping section contains 5 theoretical stages of Sulzer MellapakPlus 452Y structured packing and a HETP of 13 inches.

The distillation column operates at a top vacuum (at the condenser) of 39 torr, a reflux ratio of 35.1 and a distillate condensing temperature of 250° F. 8.5% of the liquid coming from the rectification section is sent to the pre-fractionator side of the dividing wall. The bottoms temperature is 441° F. The maximum flood (%) is 71% in the stripping section. The required reboiler duty is 1.75 million BTU/hr.

Example 2—Separation of Feed Stream Containing n-octyl Mercaptan

Figure 3:
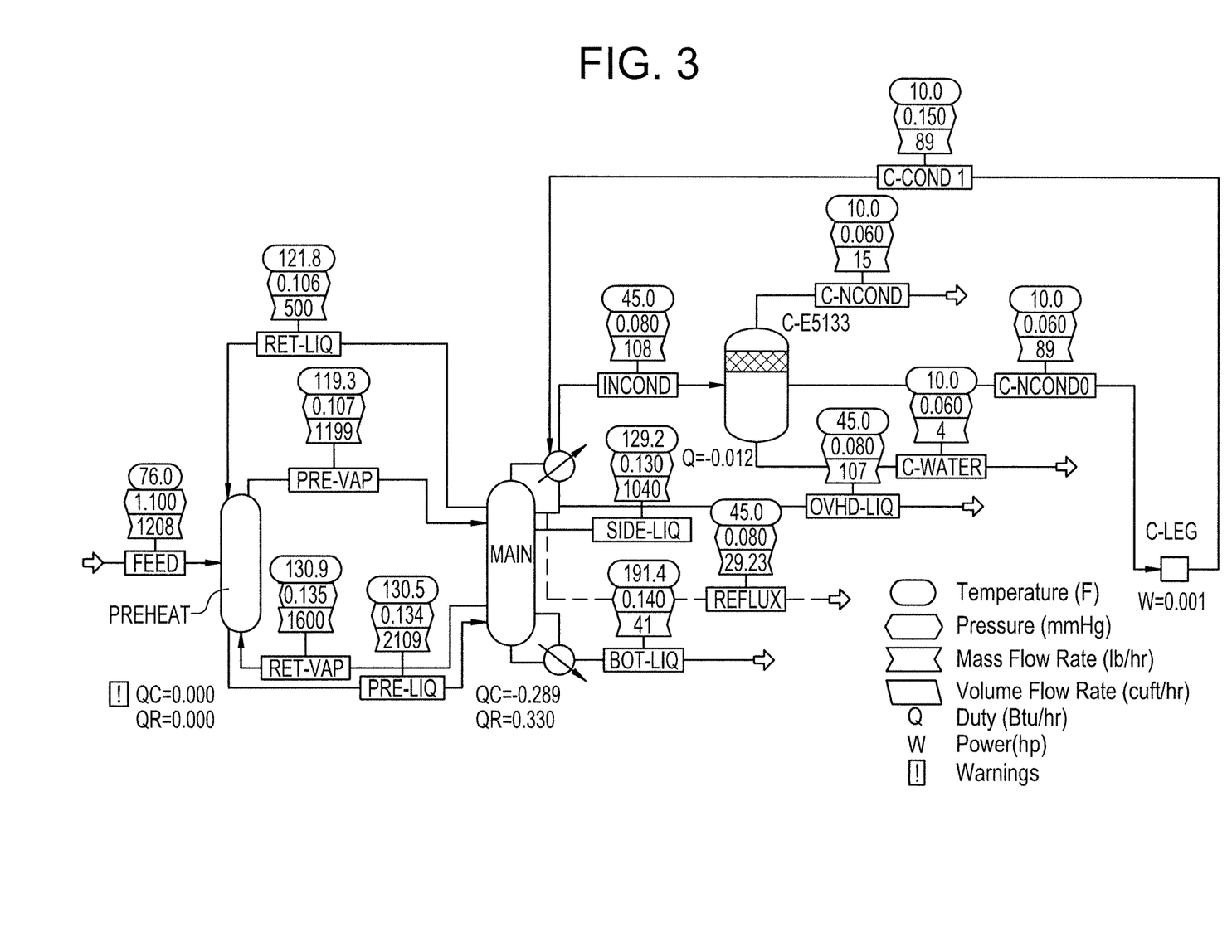
FIG. 3 is a schematic of a system for obtaining n-octyl mercaptans from a feed stream containing a mixture of mercaptans and thiophenes in accordance with aspects of the present invention.

The objective is to obtain n-octyl mercaptan (NOM) from a feed stream having a mass flow rate of 1208 kilograms per hour and containing 86.6 wt % n-octyl mercaptan (NOM), 1.1 wt % s-octyl mercaptan (SOM), 1.1 wt % n-decyl mercaptan (C10-SH), 6.8 wt % octene, 2.0 wt % of lights (e.g., more volatile than SOM) and 2.6 wt % of heavies (e.g., sulfides and disulfides). It is a further objective that the stream of NOM have a concentration of at least 99.0 wt % and contain less than 0.5 wt % of SOM, while recovering of 99 wt % of the NOM from the feed stream. The model of the distillation column employed herein is illustrated in FIG. 3.

The objectives are achieved by utilizing a system according to aspects of the invention. The system is modeled using methods similar to Example 1. The system employs a distillation column with the following parameters. The distillation column has a total of 45 theoretical stages, including a reboiler and condenser.

The top rectification section has 19 theoretical stages. The above-feed fractionator section contains 7 theoretical stages. The below-feed fractionator section contains eight theoretical stages. The region above the side draw stream in the side draw section contains 18 theoretical stages. The region below the side draw stream in the side draw section contains 2 theoretical stages. The stripping section contains 4 theoretical stages.

The distillation column operates at a top vacuum (at the condenser) of 80 mbar abs, a reflux ratio of 13.5, and a condensing temperature of 45° C. 15% of the liquid coming from the rectification section is sent to the feed side section. The bottoms temperature is 191° C. The required reboiler duty is 0.330 Gcal/h.

Comparative Example 1—Separation of Feed Stream Containing n-dodecyl Mercaptan

Figure 4:
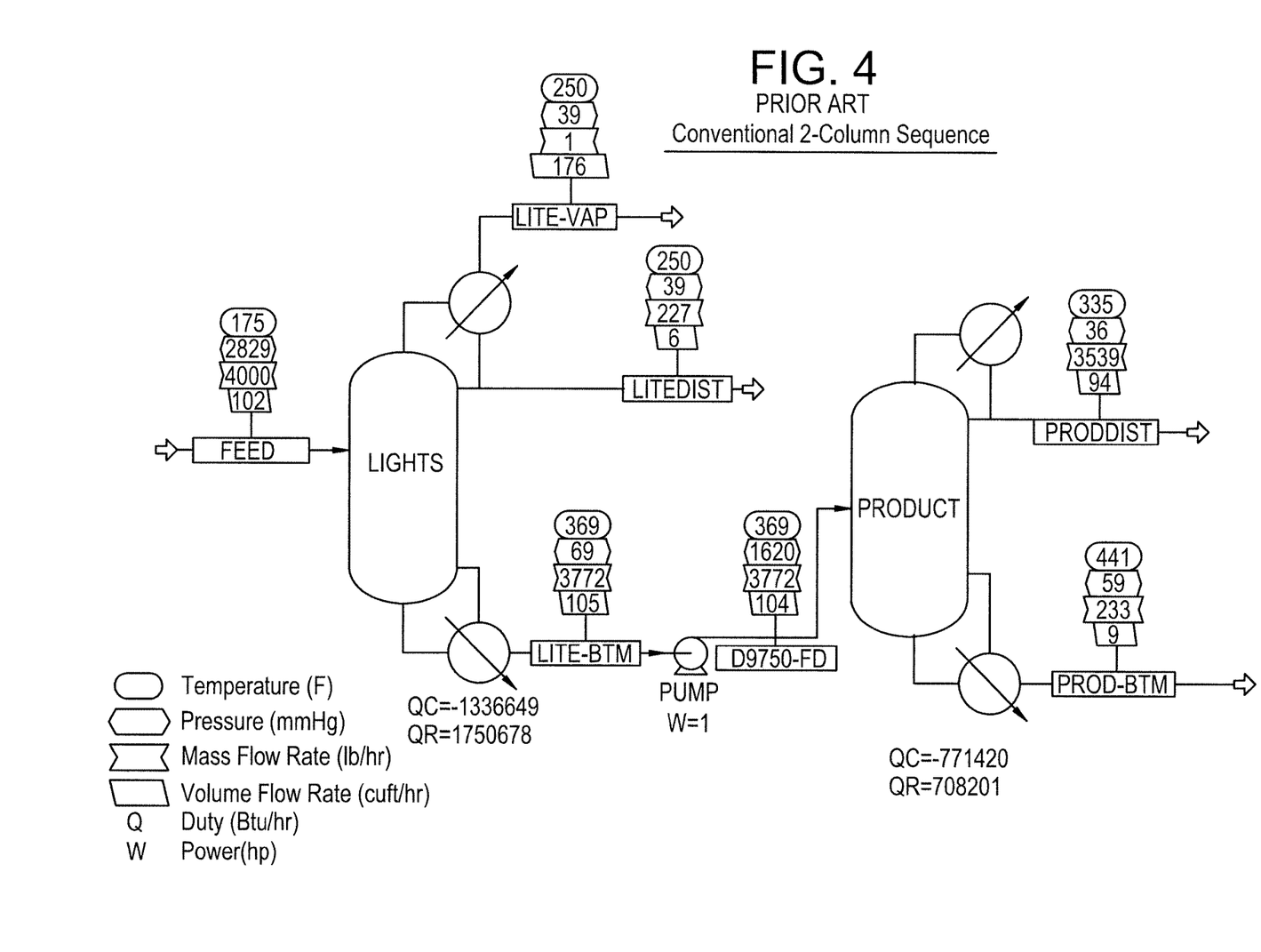
FIG. 4 is a schematic of a conventional system for obtaining n-dodecyl mercaptans from a feed stream containing a mixture of mercaptans and thiophenes.

The same objectives as Example 1 are achieved using traditional systems for separating mercaptans and thiophenes. The system employs a traditional two column distillation process, where the more volatile components are removed in the first column and the n-dodecyl mercaptan is obtained from the second column, as illustrated in FIG. 4.

The first column has a diameter of four feet and contains 55 theoretical stages, including a reboiler and condenser. The theoretical stages contain Sulzer MellapakPlus 452Y structured packing and a HETP of 13 inches. The first column operates at a top vacuum (at the condenser) of 39 torr, a reflux ratio of 33.3, and a condensing temperature of 250° F. The bottoms temperature is 366° F. The maximum flood (%) is 79%, in the region below the feed. The required reboiler duty is 1.75 million BTU/hr.

The second distillation column is three feet in diameter, and has 30 theoretical stages, including a reboiler and a condenser. The theoretical stages are designed to be Sulzer MellapakPlus 452Y structured packing, with a HETP of 13 inches. The second distillation column operates at a top vacuum (at the condenser) of 36 torr, a reflux ratio of 0.6, and the condensing temperature is 335° F. The bottoms temperature is 441° F. The maximum flood (%) is 72%, in the region above the feed. The required reboiler duty is 0.71 million BTU/hr. The combined reboiler duties of the two columns is 2.46 million BTU, which is 40.6% greater than the reboiler duty of the DWC in Example 1.

Comparative Example 2—Separation of Feed Stream Containing n-octyl Mercaptan

Figure 5:
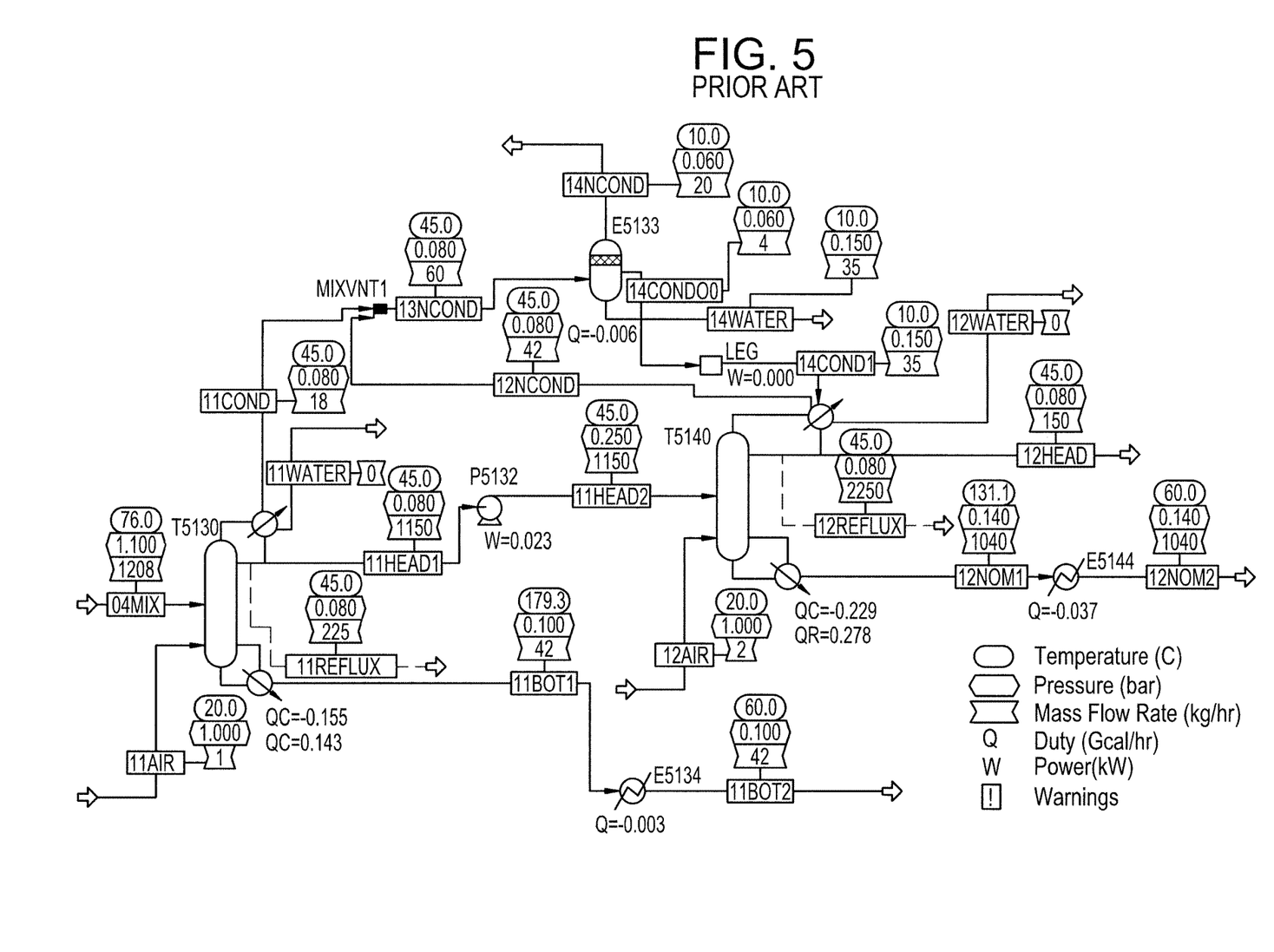
FIG. 5 is a schematic of a conventional system for obtaining n-octyl mercaptans from a feed stream containing a mixture of mercaptans and thiophenes.

The same objectives as Example 2 are achieved using traditional systems for separating mercaptans and thiophenes. The system employs a traditional two column distillation process, where the more volatile components are removed in the first column and the n-dodecyl mercaptan is obtained from the second column, as illustrated in FIG. 5.

The first distillation column is configured to remove the C10-SH and the less volatile components by way of the bottoms stream, and send its distillate (containing SOM, NOM and light components) as feed to the second column. The second distillation column recovers the NOM in the bottoms stream and removes SOM and more volatile components by way of the distillate.

The distillation column has a diameter of 0.65 meters and 15 theoretical stages, including the reboiler and condenser. The theoretical stages contain Sulzer MellapakPlus 250X structured packing, with a HETP of 500 mm. The column operates at a top vacuum (at the condenser) of 80 mbar abs, a reflux ratio of 0.2, and the condensing temperature is 45° C. The bottoms temperature is 179° C. The maximum flood (%) is 60%, in the region below the feed. The required reboiler duty is 0.143 Gcal/h.

The second distillation column has a diameter of 1.1 meters and 35 theoretical stages, including the reboiler and condenser. The theoretical stages contain Sulzer MellapakPlus 750Y structured packing and had a HETP of 200 mm. The second distillation column operates at a top vacuum (at the condenser) of 80 mbar abs and a reflux ratio of 15, and the condensing temperature is 45° C. The bottoms temperature is 131° C. The maximum flood (%) is 75%, in the region above the feed. The required reboiler duty is 0.278 Gcal/h. The combined reboiler duties of the two columns is 0.421 Gcal/h, which is 27.6% greater than the reboiler duty of the DWC in Example 2.

Comparison of Example 1 and Comparative Example 1

Table 1, shown below, provides various operational parameters for the systems employed in Example 1 and Comparative Example 1. Notably, the system of Example 1 provides the following advantages over the system employed in Comparative Example 1:

29% lower energy consumption;
11% higher capacity (based on the highest % maximum flood in each region of the distillation column);
The product is not exposed to high (reboiler) skin temperatures;
12% fewer total theoretical stages to accomplish the recovery and purity objectives;
Only one column and ancillary equipment is required, substantially reducing the required capital investment; and
Higher product quality (half the residual NTM impurity).
Table 1.

The product is not exposed to high (reboiler) skin temperatures;
10% fewer total theoretical stages to accomplish the recovery and purity objectives; and
Only one column and ancillary equipment is required, substantially reducing the required capital investment.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A process for separating as a side draw stream a primary mercaptan of 4-16 carbon chain length and optionally thiopene from a feed stream, said feed stream containing a mixture comprising primary, secondary and tertiary mercaptans using a distillation column, the process comprising:

providing one or more distillation columns with said feed stream, the distillation column having a rectification section, a stripping section, and a feed side section

|  | Conventional | | | DWC | | |
|---|---|---|---|---|---|---|
| Section | Light-Ends Column | Product Column | Overall or Equivalent | Pre-Fractionator | Main | Overall or Equivalent |
| Theoretical Stages | | | | | | |
| Above-feed | 20 | 23 | | | | |
| Below Feed | 33 | 5 | | | | |
| Above Wall | | | | | 18 | |
| Divided section above feed | | | | 19 | 19 | |
| Divided section below feed/above side-draw | | | | 16 | 16 | |
| Divided section below side-draw | | | | 15 | 15 | |
| Below Wall | | | | | 5 | |
| Equivalent Diameter (feet) | | | | | | |
| Above-feed | 4.0 | 3.0 | | | | |
| Below Feed | 4.0 | 3.0 | | | | |
| Above Wall | | | | | 4.0 | 4.0 |
| Divided section above feed | | | | 2.4 | 3.2 | 4.0 |
| Divided section below feed/above side-draw | | | | 2.6 | 3.0 | 4.0 |
| Divided section below side-draw | | | | 2.8 | 2.8 | 4.0 |
| Below Wall | | | | | 4.0 | 4.0 |
| Mellapack Plus Packing | | | | | | |
| Above-feed | 452Y | 452Y | | | | |
| Below Feed | 452Y | 752Y | | | | |
| Above Wall | | | | | 452Y | |
| Divided section above feed | | | | 752Y | 252Y | |
| Divided section below feed/above side-draw | | | | 252Y | 252Y | |
| Divided section below side-draw | | | | 252Y | 252Y | |
| Below Wall | | | | | 452Y | |
| Max % Flood | | | | | | |
| Above-feed | 59 | 72 | 72 | | | |
| Below Feed | 79 | 40 | 79 | | | |
| Above Wall | | | | | 60 | 60 |
| Divided section above feed | | | | 43 | 62 | 62 |
| Divided section below feed/above side-draw | | | | 70 | 68 | 70 |
| Divided section below side-draw | | | | 63 | 65 | 65 |
| Below Wall | | | | | 71 | 71 (11% More capacity) |
| Reboiler Duty (MM BTU/hr) | 1.751 | 0.708 | 2.459 | | | 1.751 (29% Less energy) |
| NDM Product Purity (wt %) | | | 99.59% | | | 99.58% |
| ppm NTM in NDM Product | | | 80 | | | 39 |
| % NDM Recovery | | | 99.00% | | | 99.03% |

Comparison of Example 2 and Comparative Example 2

The system of Example 2 provides the following advantages over the system employed in Comparative Example 2:

21% lower energy consumption;

separated from a side draw section by a dividing wall that extends from the rectification section to the stripping section;

condensing a vapor from the distillation column with a condenser and heating a liquid from the distillation column with a reboiler;

removing a distillate stream from a top region of the distillation column;

removing said side draw stream of a primary mercaptan of 4-16 carbon chain length from a side region of the distillation column; and removing a bottoms stream from a bottom region of the distillation column.

2. The process of claim 1, wherein one or two distillation columns are utilized.

3. The process of claim 1, wherein one distillation column is utilized.

4. The process of claim 1, wherein compounds sent to the bottoms stream only pass through one reboiler.

5. The process of claim 1, wherein the feed side section comprises less than 40% of the column cross sectional area.

6. The process of claim 1, wherein more than 90% of the mercaptans pass one or fewer times through one or more reboilers.

7. The process of claim 6, wherein the distillate stream and the side draw stream together contain the majority of mercaptans from the feed stream.

8. The process of claim 1, wherein the reboiler is operated at a temperature of 240 degrees Celsius or less.

9. The process of claim 1, wherein the condenser utilizes a coolant, and the coolant is selected from the group consisting of cooling air and cooling water.

10. The process of claim 1, wherein a liquid coming from the rectification section is controllably distributed to the feed side section and the side draw section of the distillation column.

11. The process of claim 10, wherein less than 10% by volume of the liquid coming from the rectification section enters the feed side section.

12. The process of claim 1, wherein a height of the dividing wall is between 35% and 80% of a height of the distillation column.

13. The process of claim 1, wherein the dividing wall extends more than 45% and less than 80% of one or more theoretical stages of the distillation column.

14. The process of claim 1, wherein the dividing wall extends more than 55% and less than 70% of the theoretical stages of the distillation column.

15. The process of claim 1, wherein the dividing wall extends more than 60% and less than two thirds of the theoretical stages of the distillation column.

* * * * *